United States Patent [19]
Baechler et al.

[11] Patent Number: 5,501,100
[45] Date of Patent: Mar. 26, 1996

[54] DEVICE FOR MEASURING THE MASS OF FIBER SLIVERS

[75] Inventors: François Baechler, Wermatswil; Klaus Strehler, Zürich; Isidor Harzenmoser, Wallisellen; Jürg Zehr, Uster, all of Switzerland

[73] Assignee: Zellweger Luwa AG, Switzerland

[21] Appl. No.: 264,334

[22] Filed: Jun. 23, 1994

[30]     Foreign Application Priority Data

Jun. 23, 1993 [CH]   Switzerland ................ 01886/93

[51] Int. Cl.⁶ .................. G01N 33/36; G01B 121/04; G01B 21/12; G01B 13/00
[52] U.S. Cl. ................ 73/37.7; 73/865; 73/160; 19/239
[58] Field of Search ............ 73/865, 160, 37.7, 73/865–868; 19/239, 240, 241, 300

[56]         References Cited

U.S. PATENT DOCUMENTS

| | | | |
|---|---|---|---|
| 3,158,291 | 11/1964 | Lytton et al. | 222/39 |
| 3,435,673 | 4/1969 | Felix | 73/37.7 X |
| 3,710,421 | 1/1973 | Tooka | 73/37.7 X |
| 3,722,260 | 3/1973 | Staheli | 73/37.7 |
| 3,854,330 | 12/1974 | Wildbolz | 73/37.7 X |
| 3,984,895 | 10/1976 | Grice, Jr. | 73/574 X |
| 4,121,450 | 10/1978 | Zurcher | 73/37.6 X |
| 4,122,703 | 10/1978 | Davis | 73/37.7 |
| 4,206,823 | 6/1980 | Krull | 19/240 X |
| 4,791,706 | 12/1988 | Wiening et al. | 19/105 |
| 4,812,993 | 3/1989 | Konig et al. | 19/239 X |
| 4,864,853 | 8/1989 | Grunder et al. | 73/160 |
| 5,014,395 | 5/1991 | Stäheli et al. | 19/240 X |
| 5,159,840 | 11/1992 | Leifeld | 73/865.8 X |
| 5,270,787 | 12/1993 | Shofner et al. | 73/160 X |
| 5,351,374 | 10/1994 | Nabulon et al. | 73/37.7 X |

OTHER PUBLICATIONS

"Autolevelling Systems at Carding and Drawing from a Technological Point of View", *USTER* News Bulletin, No. 30, Aug. 1982, 22 pages.

Index of the USTER News Bulletin Issues 1–30 (English Edition) 2 pages published 1982.

*Primary Examiner*—Thomas P. Noland
*Attorney, Agent, or Firm*—Burns, Doane, Swecker & Mathis

[57]         ABSTRACT

A device for measuring the mass of fiber slivers contains an entry part for the fiber sliver to be measured and a measuring part adjoining the entry part. Arranged on the measuring part are two measuring members working on different measurement principles, specifically a so-called fiber-sliver mechanically, and so-called active-pneumatic measuring member for measuring the pneumatic pressure generated by the fiber sliver at a contraction. In addition to measuring the mass of fiber slivers, the device can be used for obtaining a characteristic variable for their composition or for separate regulation and monitoring in a control stage.

14 Claims, 4 Drawing Sheets

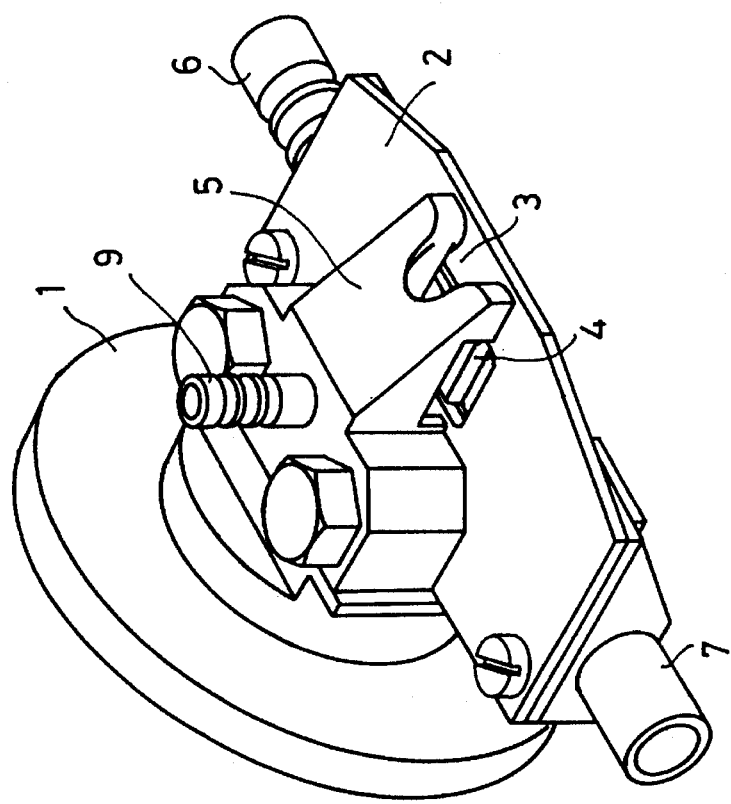
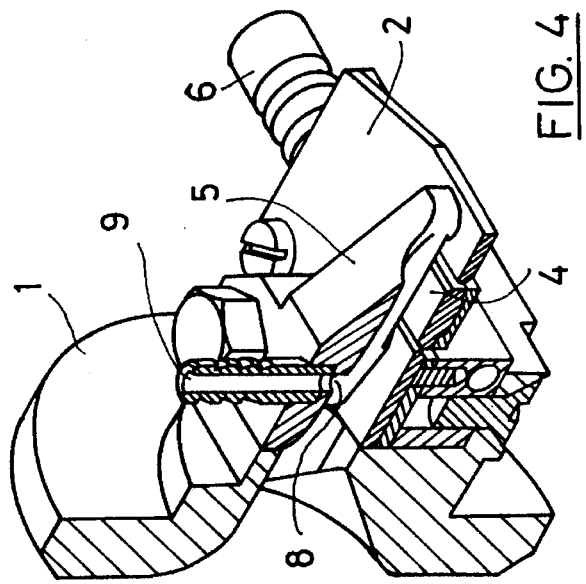
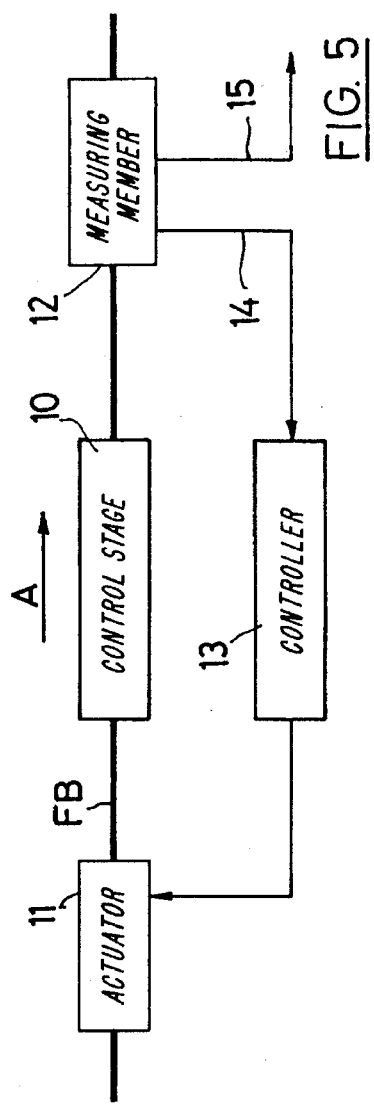

DEVICE FOR MEASURING THE MASS OF FIBER SLIVERS

FIELD OF THE INVENTION

The present invention relates to a measuring device for use in connection with fibre slivers. More particularly, the present invention pertains to a device for measuring the mass or substance cross-section of fibre slivers, with an entry part for the fibre sliver to be measured and with a measuring part adjoining the entry part and having a measuring member.

BACKGROUND

Devices of this type are used in systems for compensating sliver-weight fluctuations and quality-data acquisition on machines producing fibre slivers and serve to keep the yarn-fineness fluctuations so small that they do not cause any disturbance in the finished fabric. The main differences in known regulating systems are in the measuring member, of which essentially three types are known, namely the so-called active-pneumatic measuring member, the roller-measurement system and the fibre-pressing system. With respect to the first two measuring members, attention is drawn to the USTER News Bulletin No. 30, 1982, and with respect to the last-mentioned measuring member, attention is directed to U.S. Pat. No. 4,864,853.

Common to all of the various measuring members is the fact that, on the one hand, in addition to the dependence on the fibre-silver mass, they also have further, usually negligible dependencies relevant to textiles. On the other hand, these measuring members allow only the measurement of the fibre-silver mass. When a further property of the fibre silver is to be monitored or measured, it is then necessary to use an additional measuring member which, however, as a rule has to be located at another measuring point as a result of space constraints.

OBJECT AND SUMMARY OF THE INVENTION

The invention provides a device of the type mentioned in the introduction in which any influence of secondary variables, with the exception of the fibre-sliver mass, is eliminated, but which nevertheless allows conclusions to be drawn as to these secondary variables.

This object is achieved, according to the invention, in that there are provided on the measuring part two measuring members for the fibre-sliver mass which work on different measurement principles and of which one has a means for measuring the pneumatic pressure generated by the fibre sliver at a contraction and the other has a measuring beam sensing the fibre sliver mechanically.

Because two measuring members are used for one and the same variable, the measuring system acquires redundancy, thus allowing, on the one hand, the elimination of the influence of the secondary variables and, on the other hand, some automatic checking of the measuring system. As a result of the use of the two measuring members, it becomes possible to make a statement or draw a conclusion with regard to the secondary variables. Since the two measuring members can be installed at virtually one and the same measuring point, the comparability of the measurement results is ensured, this being important for eliminating the influence of the secondary variables.

With respect to the statements or conclusions regarding the secondary variables, it should be noted that, as a rule, these will not represent quantitative measurement results of a specific parameter, but a measure of a characteristic variable which supplies on-line a statement regarding the composition of the fibre sliver examined. A preferred embodiment of the device according to the invention includes two measuring members, one of which is a so-called active-pneumatic and the other of which is a so-called fibre-pressing measuring member.

The invention relates, furthermore, to a use of the aforementioned device for obtaining a characteristic variable for the composition of the recorded fibre sliver. In this regard, the signals of the two measuring members are examined for mutual deviations characteristic of specific parameters influencing the composition.

The invention relates, moreover, to a use of the aforementioned device for separate regulation and monitoring in a control stage. In such a use, the signal of one, preferably the active-pneumatic measuring member, is used for sliver regulation and the signal of the other, preferably the fibre-pressing measuring member, is used for sliver monitoring.

BRIEF DESCRIPTION OF THE DRAWING FIGURES

The invention is explained in more detail below by means of exemplary embodiments and the accompanying drawing figures in which like elements bear like reference numerals and wherein:

FIG. 3 is a perspective view of a second exemplary embodiment of a device according to the invention;

FIG. 4 is an axial longitudinal sectional view through the exemplary embodiment of FIG. 3;

FIG. 5 shows a basic diagram of a stage regulation with a device according to the invention as a measuring member;

DETAILED DESCRIPTION OF THE PREFERRED EMBODIMENTS

Figure 2:
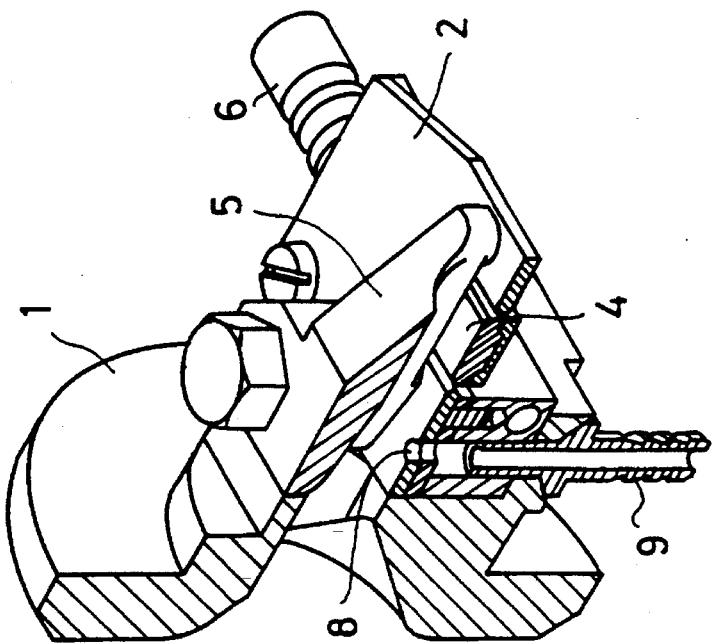
FIG. 2 is an axial longitudinal sectional view through the exemplary embodiment of FIG. 1.
Figure 1:
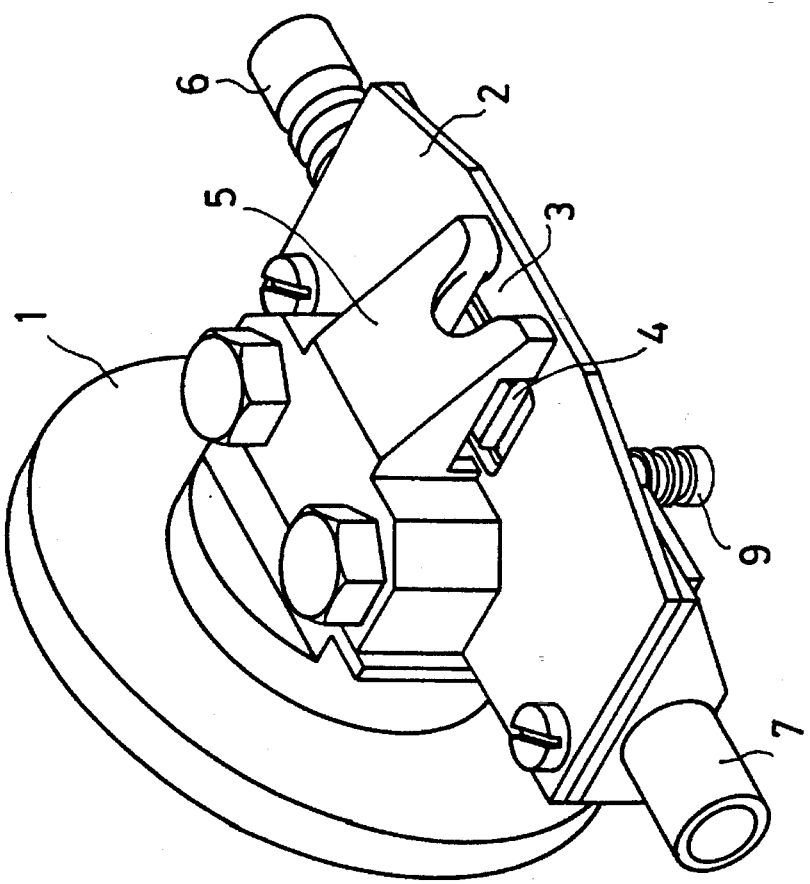
FIG. 1 is a perspective view of a first exemplary embodiment of a device according to the invention.

Some of the features of the measuring member shown in FIGS. 1 to 4 correspond to features of the device described in U.S. Pat. No. 4,864,853, the entire disclosure of which is incorporated herein by reference. The measuring member contains, in a known way, an entry part 1 for the precompaction of the fibre sliver and a measuring part 2 fastened to the entry part 1. The measuring part 2 possesses a measuring channel 3 which is limited by a measuring plane and by a gutter-shaped sliver guide. The measuring plane contains a measuring beam 4 formed by a leaf spring equipped with strain gauges, and the sliver guide is worked out of a guide part 5 fastened exchangeably to the measuring part 2.

The measuring part 2 moreover contains a connecting nipple 6 for cooling and cleaning the measuring part by means of compressed air, the cooling taking place continuously and the cleaning intermittently. An electrical connection for recording the signal of the measuring beam 4 is designated by reference numeral 7.

All of the parts mentioned hitherto are known from the fibre-pressing measuring system which is described in the aforementioned U.S. Pat. No. 4,864,853 and the sensor of which is formed by the measuring beam 4. The measuring member illustrated in the drawing figures also has, in addition, an active-pneumatic measuring member of the type described in U.S. Pat. No. 3,435,673, by means of which the pressure generated by the moved fibre sliver at a contraction is evaluated as a measured variable. The contraction is located in the region between the entry part 1 and the measuring beam 4, and the arrangement for evaluating the pressure comprises a bore 8 in the respective wall of the guide channel 3 and a connection, leading away from this bore, for recording the active-pneumatic measurement signal.

The two embodiments of FIGS. 1, 2 and 3, 4 differ in that the bore 8, in the first case, is made in the measuring plane containing the measuring beam 4 and, in the second case, is made in the guide part 5 located opposite the measuring beam 4.

In the following operating description, the designation FP is used to identify the function and the elements of the fibre-pressing measuring system (measuring channel 3, measuring beam 4, guide part 5) and the designation AP is used to identify the function and the elements of the active-pneumatic measuring system (measuring channel 3, bore 8, connection 9).

The measuring beam 4 (which could also be designated as a measuring diaphragm) of the FP measuring part supplies a signal as a function of the compression of the fibre sliver in the measuring channel 3. This signal is amplified by a pre-amplifier connected to the connection 7, thus resulting in the FP measurement signal $S_{FP}$ which is a function of the measuring-channel cross-section $Q_k$, the fibre-sliver mass $B_m$, the sliver speed $B_v$, and the fibre-sliver composition $B_z$:

$$S_{FP}=f(Q_k, B_m, B_v, B_z)$$

By means of the size of the measuring-channel cross-section, the optimum condition of the FP measurement function is determined as a function of the mean fibre-sliver mass. With a constant sliver speed $B_v$, and a correct measuring-channel cross-section $Q_k$, the FP signal varies according to the following equation:

$$\delta S_{FP}=K_{fpm}\cdot\delta B_m+K_{fpz}\cdot\delta B_z (\delta X \equiv \Delta X/X)$$

$K_{fpm}$: FP conversion factor of the fibre-sliver mass $K_{fpz}$: FP conversion factor of the fibre-sliver composition The compression of the fibre sliver in the measuring channel generates a pneumatic pressure which is recorded at the connection 9 via the bore 8 and which is convened into an electrical signal $S_{AP}$ by means of a pressure transducer. This signal is a function of the fibre-sliver mass $B_m$, the sliver speed $B_v$, the measuring-channel cross-section $Q_k$ and the fibre fineness $B_f$:

$$S_{AP}=f(Q_k, B_m, B_v, B_f)$$

With a constant sliver speed $B_v$, and with the measuring-channel cross-section $Q_k$ used for the FP function, the AP signal varies according to the following equation:

$$\delta S_{AP}=K_{apm}\cdot\delta B_m+K_{apf}\cdot\delta B_f$$

$K_{apm}$: AP conversion factor of the fibre-sliver mass $K_{apf}$: AP conversion factor of the fibre fineness The two signals of the measuring part 2 thus give particulars of three different properties of a fibre sliver, namely the fibre-sliver mass variations $\delta B_m$ the fibre-fineness variations $\delta B_f$ the fibre-sliver composition variations $\delta B_z$.

By means of the series connection of the two independent and different measurement systems at one measuring point, it thus becomes possible, in addition to measuring the fibre-sliver mass, to make a statement or draw a conclusion, summarized in a characteristic variable, regarding further textile parameters, especially regarding fibre fineness and fibre-sliver composition. This characteristic variable, which also includes further parameters, such as fibre length, bulk, parallelization, short-fibre fraction, fraction of the floating fibres and specific gravity, supplies a qualitative indication as to the composition of the recorded fibre sliver.

The series connection of the measurement systems thus allows, for example, the optimum setting of the drafting-unit distance, since an increase in floating fibres causes a characteristic rise in the FP measurement signal.

| | Signals | | Fibre sliver | | | |
|---|---|---|---|---|---|---|
| Case | $\delta S_{FP}$ | $\delta S_{AP}$ | $\delta B_m$ | $\delta B_f$ | $\delta B_z$ | Probability |
| 1 | 0 | 0 | 0 | 0 | 0 | low |
| 2 | 0 | $\neq 0$ | 0 | $\neq 0$ | 0 | high |
| 3 | $\neq 0$ | 0 | 0 | 0 | $\neq 0$ | low |
| 4 | $\neq 0$ $x=y$ | $\neq 0$ | $\neq 0$ | 0 | 0 | very high |
| 5 | $\neq 0$ $X=Y$ | $\neq 0$ | 0 or $\neq 0$ | $\neq 0$ $Q=R$ | $\neq 0$ | very low |
| 6 | $\neq 0$ $X \neq Y$ | $\neq 0$ | $\neq 0$ | $\neq 0$ $\neq \delta B_z$ | $\neq 0$ $\neq \delta B_f$ | medium |

The evaluation of the FP/AP signals can be carried out according to the diagram indicated in the above table, an indication being given for each of the various cases of the FP/AP signal as to which of the three properties mentioned could exhibit a variation and how high the probability is that the individual cases will occur. The designations "0" in the above table indicates no deviation in the signal and respective property while the designation "$\neq 0$" indicates some deviation. The probability identifies the likelihood that a given situation or case will occur. Thus, for example, the probability is low that a situation in case 1 (i.e., $\delta S_{FP}=\delta S_{AP}=0$) will occur very often, but it is highly probable that a situation as in case 2 (i.e., $\delta S_{FP}=0$; $\delta S_{AP} \neq 0$) will occur often. In cases 1 to 4, the various deviations can be recognized clearly and localized.

In the above table, the symbols X and Y used in the cases 4 to 6 designate respectively the quotients $\delta S_{AP}/K_{apm}$ and $\delta S_{FP}/K_{fpm}$; the symbols Q and R used in case 5 denote respectively the values $\delta B_z \cdot K_{fpz}/K_{fpm}$ and $\delta B_f K_{apf}/K_{apm}$.

The combined measuring member described (combination measuring member) can be used, on the one hand, as a measuring member for determining the quality data of a fibre sliver and, on the other hand, as a measuring member for regulating and equalizing the mass of a fibre sliver. In the latter case, irregularities are not only recorded, but also initiate corresponding control operations (see, in this respect, for example the USTER News Bulletin No. 30, 1982). Since the known measuring members respond not only to variations in the fibre-sliver mass, but, as shown, also to those in the fibre-fineness (AP measuring member) or in the fibre-sliver composition (FP measuring member), in addition to the measuring member a further monitoring member is required for checking the regulation. For example, if an AP measuring member is used, then, a change in the fibre fineness would bring about a regulating step in the direction of a variation in the fibre-sliver mass, and this would not only be false, but would not even be noticed at all by the measuring member. In contrast, if the combination measuring member described above, with the AP and the FP measuring member, is used, there is no need for the additional monitoring member.

FIG. 5 shows a basic diagram of a stage regulation which is equipped with a combination measuring member and through which a fibre sliver FB runs in the direction of the arrow A. The stage regulation consists essentially of a control stage 10, an actuator 11 preceding this control stage 10, of a combination measuring member 12 following the control stage 10 and a controller 13 arranged between the measuring member 12 and the actuator 11.

If the fibre sliver FB has a deviation (disturbance variable), this is detected by the combination measuring member 12 which transmits a corresponding signal for sliver regulation to the controller 13 via a regulation line 14. The controller 13 in turn calculates the necessary control variable and actuates the actuator 11 accordingly. The signal for sliver regulation can, for example, be the AP measurement signal. At the same time, the second measuring member of the combination measuring member 12, in this case the FP measuring member, serves for sliver monitoring and supplies a corresponding signal on a line 15. The line 15 can be connected to a monitoring system which includes, for example, a monitor.

The combination measuring member described has the following main features:

Continuous measurement of the fibre-sliver mass by two different measuring methods which respond differently to further parameters, such as fibre fineness and fibre-sliver composition.

The comparison of the signals obtained by the two measuring methods on the one hand allows an automatic check of the measuring member and on the other hand supplies a characteristic variable which permits at least one qualitative statement regarding the composition of the recorded fibre sliver.

The possibility of using the combination measuring member for the separate regulation and monitoring functions.

By exchanging the guide part 5 on the combination measuring member, the optimum working conditions for the particular fibre sliver can be determined both for the FP and for the AP function.

Figure 6:
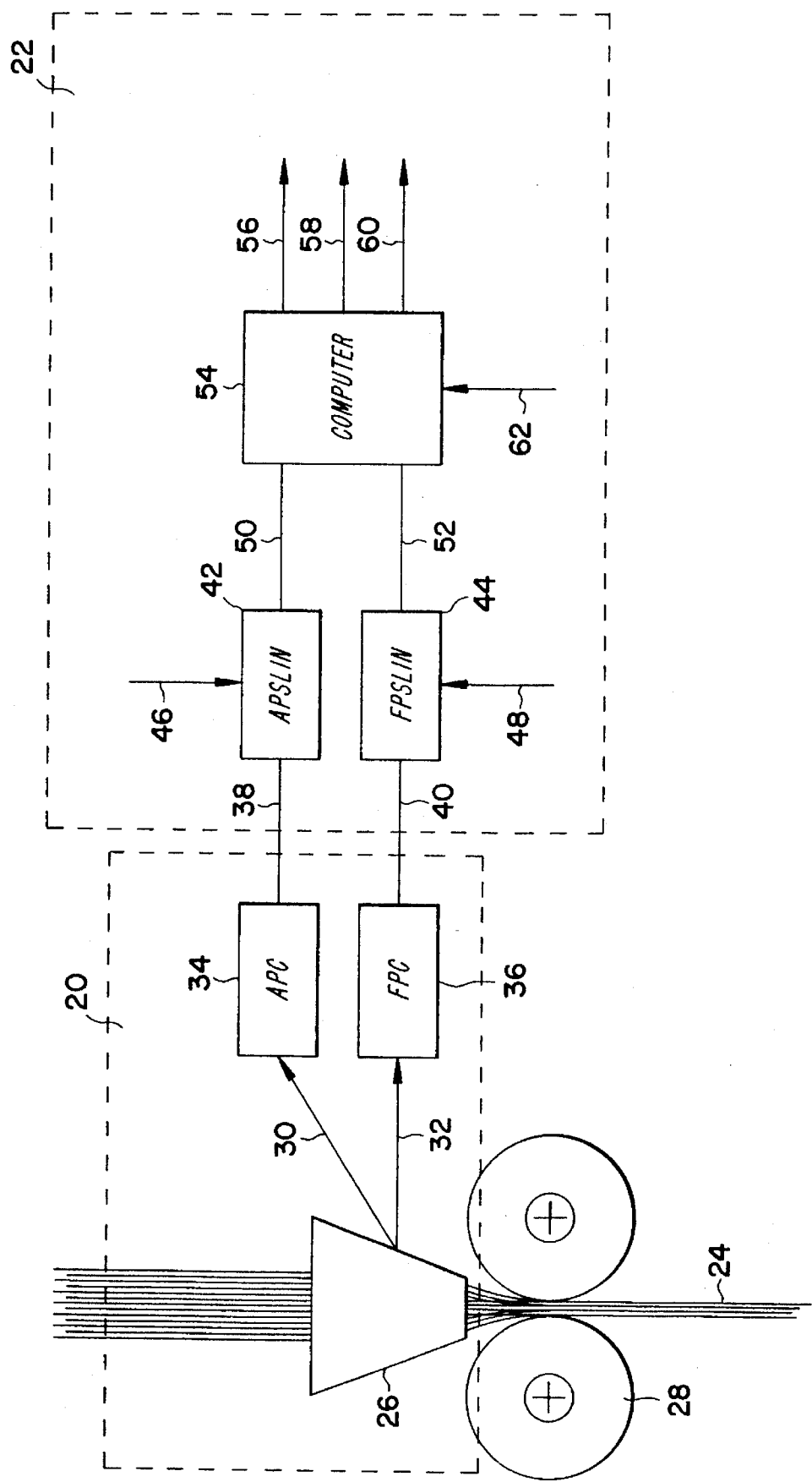
FIG. 6 is a schematic illustration of a system for processing information obtained by the measuring member and for outputting signals indicative of the characteristic variables for the composition of the recorded fibre-sliver.

With reference to FIG. 6, a system for using the measuring member described above is illustrated. The measuring member generally illustrated in FIGS. 1–4 is identified with reference numeral 26 in FIG. 6. Rollers 28 are provided to advance the fibre slivers to the measuring member 26. Two transducers 34 (pneumatic pressure only) and 36 (mechanical pressure only) are connected to the measuring member 26, and receive signals outputted from the measuring member 26. The transducers 34, 36 are connected to processors 42, 44, respectively so that signals from the transducers 34, 36 sent along lines 38, 40 are received by the respective processors 42, 44. Respective inputs 46, 48 are also connected to the processors 42, 44 for allowing the input of parameters. A computer 54 receives information from the processors 42, 44 along connection lines 50, 52. An input 62 is provided for inputting parameters into the computer 54. The computer 54 outputs information along lines 56, 58, 60 indicative of the mass-value of the fibre sliver, the fineness of the fibres of the sliver, and values related to the composition of the fibre sliver.

In operation, the values related to pressures transmitted from the measuring member 26 to the transducers 34, 36 are converted into corresponding electric signals in the transducers 34, 36. Those electrical values are then sent to the corresponding processors 42, 44 where they are linearized. That is, different characteristics are stored in the processors 42, 44 for transforming input values into output values. Those characteristics to be used are selected or modified by way of parameters which can be entered through inputs 46, 44. By way of example, such characteristics take into account specific behaviors of the pressure signals as they are output from the measuring member 26, non-linearities due to the transducers 34, 36, and the like.

Output values from the processors 42, 44 as they are present in lines 50, 52 are treated in the computer 54 according to the rules and information contained in the table set forth above. Therefore, the computer receives signals on two lines corresponding to those values presented in the second and third column of the table arranged below the heading "signals", and sends output signals as presented in the three adjacent columns below the heading "fibre sliver" which are sent over the three lines 56, 58, 60. The computer 54 is programmed in a manner that permits execution of a signal treatment, that is a relationship between input and output values as presented in the aforementioned table. For the situations identified as 1–4 in the table, quantitative predictions can also be made for output values as a function of the input values. That is, a change in input values will be reflected by a corresponding change in the output values. This is not equally true for the situations identified as 5 and 6 in the aforementioned table since those situations reflect more of a qualitative treatment only.

The output signals conveyed along lines 56, 58, 60 are the characteristic variables for the composition of the recorded fibre sliver and the two signals issued by the measuring member 26 are examined for mutual deviations characteristic of specific parameters in the computer 54 according to the table set forth above to obtain the three variables. As mentioned above, the series connection of the active pneumatic member and the fibre-pressure measuring member allows the optimum setting of the drafting unit. The distance between the drafting points can be chosen depending upon the amount of floating fibres the operator is prepared to allow in the sliver. The more such drafting points are spaced apart, the more floating fibres will be present in the sliver. The amount of floating fibres is expressed by the value in the output line 60 which, in turn, is a function of the value of the signal in lines 32, 40, 52. The sliver monitoring can also take place in a way as expressed by the functions described in the table set forth above. Monitoring in this case tells something about the effects on the sliver and the regulation performed in the processor 42 appears to have. The FP signal is a quicker signal which is thus better used for monitoring while the AP signal does not vary rapidly with time and so is better suited for regulation.

Figure 7:
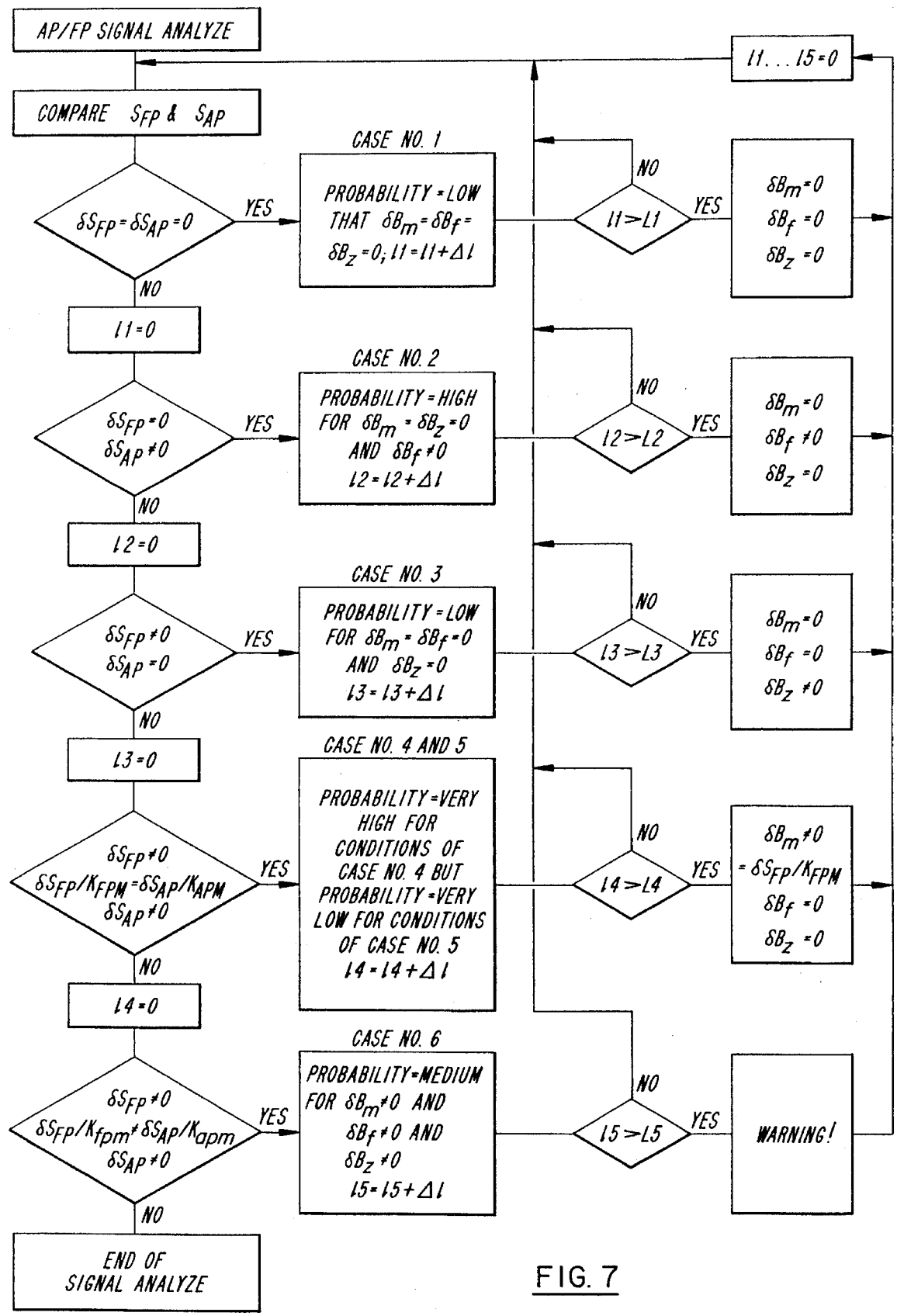
FIG. 7 is a flow chart illustrating the analysis of signals derived from information obtained by the measuring member.

FIG. 7 sets forth a flow chart illustrating the signal analysis for the AP and FP signals derived from information obtained by the measuring member. As illustrated, the signals $\delta S_{FP}$ and $\delta S_{AP}$ are initially compared and if both are zero, then $\delta B_m$, $\delta B_f$ and $\delta B_z$ will all be zero too. This is in fact case no. 1 shown on the table set forth above and the probability that such a situation will arise is low. This comparison is checked for yarn samples having an initial length of zero, the length being incremented after each comparison. Thus, there are ever-increasing sample lengths 11, 12 . . . In for this first test or first loop. A limit L1 is also set for the sample length and as long as the sample length 1 is smaller than L1, $\delta S_{FP}$ and $\delta S_{AP}$ are again compared and the sample length increased. These operations continue and repeat during this first loop. If 11 is greater than L1, this first case is established and the values of the fibre sliver are confirmed, namely that is $\delta B_m$, is equal to 0, $\delta B_f$ is equal to 0 and $\delta B_z$ is equal to zero.

Once $\delta S_{FP}$ or $\delta S_{AP}$ are not zero, which is rather probable or likely to happen at one time, a new loop starts with a similar procedure and with a new sample length 11 of zero, which is incremented for each performance of the loop. In the second loop, it is tested if $\delta S_{FP}$ is zero and $\delta S_{AP}$ is not zero. If this is true, case no. 2 in the table set forth above arises and $\delta B_f$ will not be zero while $\delta B_m$ and $\delta B_z$ remains zero. This is again tested several times at least until the sample length has been incremented to 12 greater than L2. If this is true, case no. 2 is established. If not, or before this is established, $\delta S_{FP}$ may prove to be not equal to zero, in which case the system proceeds on to the third loop for case no. 3. As long as the conditions for this case are met, that is $\delta S_{FP} \neq 0$ and $\delta S_{AP}=0$, case no. 3 is established.

The further loops corresponding to cases 4, 5 and 6 in the table set forth above are performed in a similar manner. In fact, a loop corresponding to case no. 5 need not be performed since it is very probable or likely not to occur. Instead of that, the highly probable case no. 4 is performed. If the conditions of case no. 6 prove to be established, a warning may be issued which can be a basis for stopping measurements or for taking other measures.

It is to be noted that the values for L1, L2, L3, L4 and L5 can be set differently depending on the probability of the case to which they are related.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. Device for measuring the mass of fiber slivers, comprising an entry part for the fiber sliver to be measured and a measuring part adjoining the entry part, said measuring part including two measuring members which operate under different measurement principles, one of the measuring members having means for measuring the pneumatic pressure generated by the fiber sliver at a contraction and the other measuring member having a measuring beam for mechanically sensing said fiber sliver.

2. Device according to claim 1, wherein said one measuring member is an active-pneumatic measuring member and the other measuring member is a fiber-pressing measuring member.

3. Device according to claim 2, wherein the measuring part has a measuring channel limited by a face which contains the measuring beam of the fiber-pressing measuring member and by a gutter-shaped sliver guide, the active-pneumatic measuring member being arranged in said measuring channel.

4. Device according to claim 3, wherein the active-pneumatic measuring member is arranged in the face of the measuring channel containing the measuring beam.

5. Device according to claim 4, wherein the two measuring members generate signals which are fed to a common evaluation stage in which comparison of the two signals is carried out.

6. Device according to claim 3, wherein the active-pneumatic measuring member is arranged in the gutter-shaped sliver-guide part of the measuring channel, said sliver-guide part being located opposite the face containing the measuring beam.

7. Use of the device according to claim 2 for obtaining a characteristic variable for the composition of the recorded fiber sliver, wherein signals output from the two measuring members are examined for mutual deviations characteristic of specific parameters influencing the composition.

8. Use according to claim 7, wherein characteristic deviations of the signal of the active-pneumatic measuring member indicate fluctuations in the fiber fineness.

9. Use according to claim 7, wherein characteristic deviations of the signal of the fiber-pressing measuring member indicate fluctuations in the fiber-sliver composition.

10. Use according to claim 7, wherein characteristic deviations of the signal of the fiber-pressing measuring member are interpreted as an indication of floating fibers, and in that such indications are used for setting the optimum drafting-unit distance of drafting points on sliver-producing machines.

11. Use of the device according to claim 2 for separate regulation and monitoring in a control stage, wherein the signal from the active-pneumatic measuring member is used for sliver regulation and the signal from the fiber-pressing measuring member is used for sliver monitoring.

12. Device for measuring the mass of a fiber sliver, comprising an entry part through which a fiber sliver passes, a measuring part adjoining the entry part, said measuring part including two measuring members which operate under different measurement principles to produce signals relating to characteristics of a fiber sliver positioned at the measuring part, a first one of the measuring members including means for measuring the pneumatic pressure generated by said fiber sliver at a contraction and a second one of the measuring members including a measuring beam for mechanically sensing said fiber sliver, and a controller for receiving signals produced by said two measuring members.

13. Device according to claim 12, wherein said first measuring member is an active-pneumatic measuring member and the second measuring member is a fiber-pressing measuring member.

14. Device according to claim 13, wherein the measuring part has a measuring channel defined by a face and a gutter-shaped sliver guide, said face containing the measuring beam of the fiber-pressing measuring member, the active-pneumatic measuring member being arranged in said measuring channel.

* * * * *